(12) United States Patent
Leon-Yip

(10) Patent No.: US 11,376,034 B2
(45) Date of Patent: Jul. 5, 2022

(54) DEVICES FOR REMOVING OBSTRUCTING MATERIALS FROM BLOOD VESSELS

(71) Applicants: STRYKER CORPORATION, Kalamazoo, MI (US); STRYKER EUROPEAN OPERATIONS LIMITED, Carrigtwohill (IE)

(72) Inventor: Garvin Leon-Yip, San Francisco, CA (US)

(73) Assignee: Stryker Corporation, Kalamazoo, MI (US)

( * ) Notice: Subject to any disclaimer, the term of this patent is extended or adjusted under 35 U.S.C. 154(b) by 158 days.

(21) Appl. No.: 16/576,694

(22) Filed: Sep. 19, 2019

(65) Prior Publication Data
US 2021/0085360 A1    Mar. 25, 2021

(51) Int. Cl.
*A61B 17/3207* (2006.01)
*A61B 17/12* (2006.01)
*A61F 2/01* (2006.01)

(52) U.S. Cl.
CPC .. *A61B 17/320725* (2013.01); *A61B 17/1204* (2013.01); *A61B 17/12109* (2013.01);
(Continued)

(58) Field of Classification Search
CPC .......... A61F 2/013; A61F 2/011; A61F 2/014; A61F 2002/016; A61F 2002/01;
(Continued)

(56) References Cited

U.S. PATENT DOCUMENTS

| 5,100,423 A | * | 3/1992 | Fearnot | A61B 17/2202 |
| | | | | 606/159 |
| 5,211,651 A | | 5/1993 | Reger et al. | |

(Continued)

FOREIGN PATENT DOCUMENTS

| CA | 2309428 | 11/1998 |
| EP | 1272110 | 1/2003 |

(Continued)

OTHER PUBLICATIONS

PCT International Search Report and Written Opinion for International Appln. No. PCT/US2020/048056 dated Oct. 28, 2020.

*Primary Examiner* — Jocelin C Tanner
(74) *Attorney, Agent, or Firm* — Vista IP Law Group, LLP

(57) ABSTRACT

A medical device includes a shaft; and a cage coupled to the shaft, the cage comprising elongated cutting members configured to cut material(s) inside a blood vessel lumen, the cage including a first end and a second end, wherein one or both of the first end and second end are moveable along a longitudinal axis of the shaft to change a distance between them; wherein the cage has a naturally expanded configuration with a first cross sectional dimension; wherein the cage is collapsible to form a collapsed configuration in response to an increase in the distance between the first end and the second end of the cage; and wherein the medical device further comprises a control configured to apply a radial force to expand the cage beyond its naturally expanded configuration with a second cross sectional dimension that is larger than the first cross sectional dimension.

22 Claims, 6 Drawing Sheets

(52) U.S. Cl.
CPC ........ *A61B 17/12136* (2013.01); *A61F 2/013* (2013.01); *A61B 2017/320716* (2013.01); *A61F 2/011* (2020.05)

(58) Field of Classification Search
CPC ..... A61F 2002/0105; A61F 2002/0108; A61B 2017/320716; A61B 2017/320725; A61B 2017/320733; A61B 2017/320741; A61B 2017/22079; A61B 2017/320775; A61B 2017/32096; A61B 17/12136; A61B 17/12109; A61B 17/1204; A61B 17/320758; A61B 17/3207; A61B 17/32056; A61B 17/22; A61B 17/221
See application file for complete search history.

(56) References Cited

U.S. PATENT DOCUMENTS

| | | | |
|---|---|---|---|
| 5,843,165 A | 12/1998 | Plaia et al. | |
| 5,904,698 A | 5/1999 | Thomas et al. | |
| 5,941,869 A | 8/1999 | Patterson et al. | |
| 6,156,043 A * | 12/2000 | Krahn | A61B 17/32056 606/110 |
| 10,105,154 B1 * | 10/2018 | Green | A61B 5/00 |
| 2001/0031981 A1 * | 10/2001 | Evans | A61B 17/221 606/200 |
| 2013/0110082 A1 * | 5/2013 | Tekulve | A61B 17/320725 604/509 |
| 2015/0359549 A1 | 12/2015 | Lenker et al. | |
| 2017/0020556 A1 * | 1/2017 | Sutton | A61B 17/320725 |
| 2017/0224375 A1 * | 8/2017 | Robertson | A61B 17/320758 |
| 2017/0238960 A1 * | 8/2017 | Hatta | A61B 17/221 |

FOREIGN PATENT DOCUMENTS

| | | |
|---|---|---|
| EP | 1452142 | 9/2004 |
| EP | 3017775 | 5/2016 |

* cited by examiner

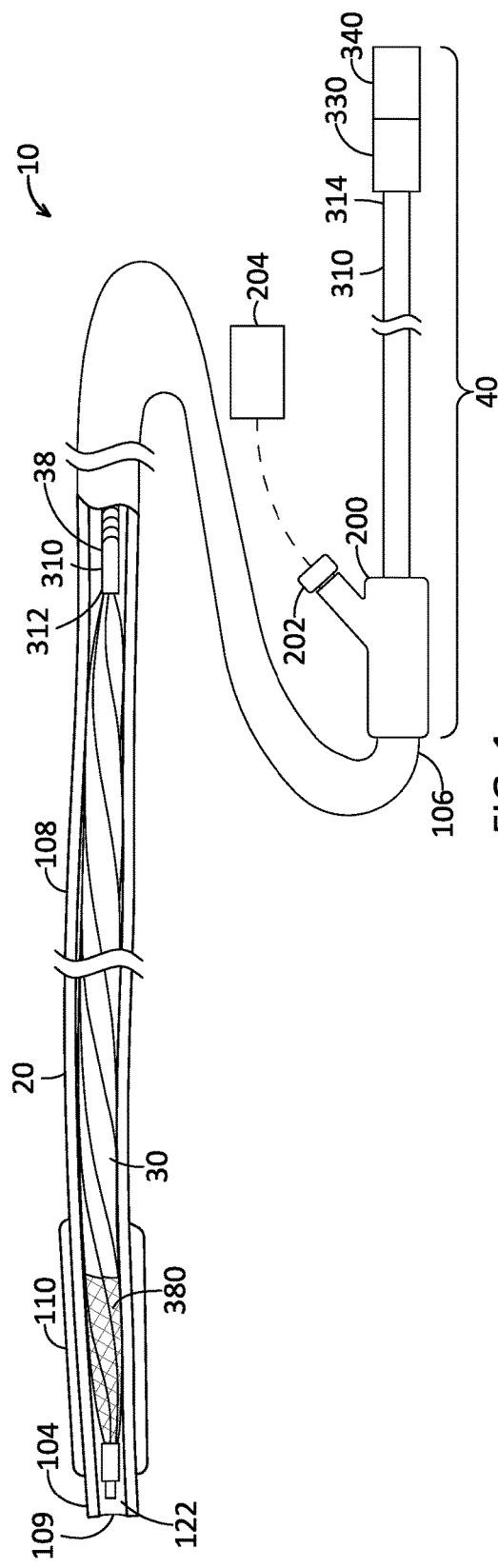
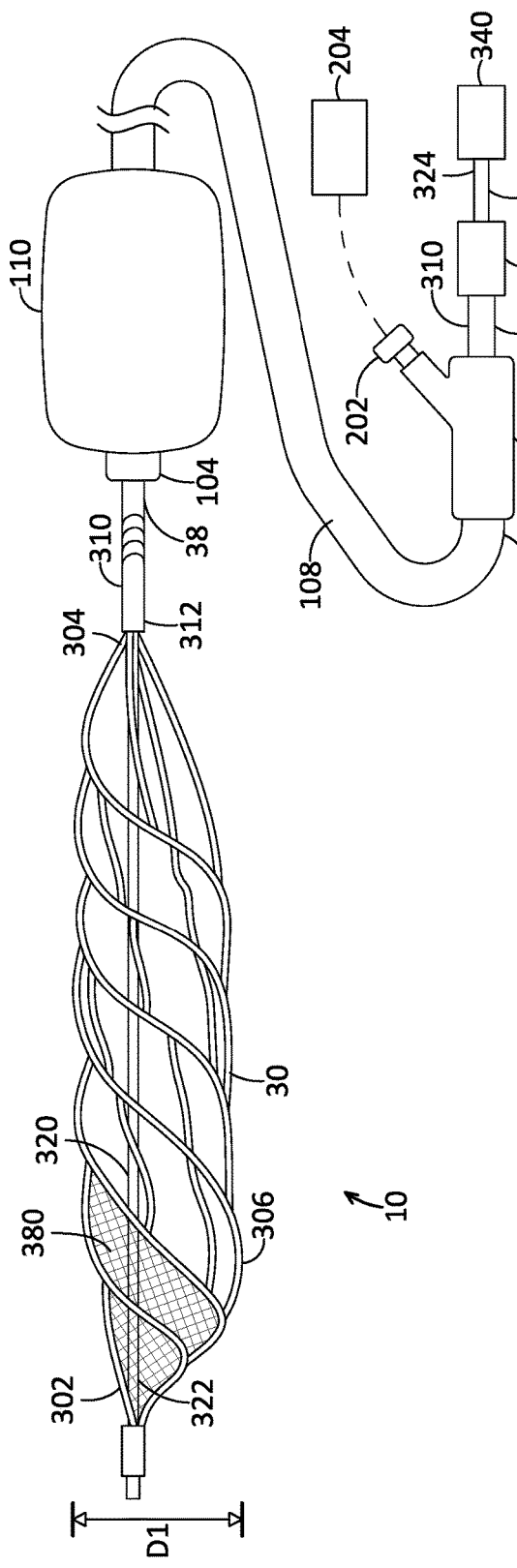
FIG. 1
FIG. 2

DEVICES FOR REMOVING OBSTRUCTING MATERIALS FROM BLOOD VESSELS

FIELD

The field of the application relates to medical devices and methods for using same to remove substance (e.g., arterial plaque) from blood vessels, and more specifically, to medical devices and methods for cutting and removing obstructing materials, such as plague, inside blood vessels.

BACKGROUND

Medical devices have been used to remove obstructing materials, such as plague, inside blood vessel lumens. Some of these devices may have a cutting element configured to cut materials along a wall of the vessel. The cutting element may have a pre-determined relaxed expanded configuration that allows the cutting element to cut the materials along the vessel wall. However, such cutting element may not be further expanded beyond the pre-determined relaxed expanded configuration during the cutting operation.

Also, existing medical devices for removing materials inside blood vessels may not have a filter that can effectively and reliably collect cut material and debris. If such material and/or debris travel away from a target site in the vessel, they may pose health risks to the patient. As such, improved devices and methods for removing materials from inside blood vessel lumens is desirable.

SUMMARY

In an exemplary embodiment of the disclosed inventions, a device for removing obstructing materials from a blood vessel lumen includes a shaft having a longitudinal axis, and a cage coupled to the shaft, the cage sized for placement in a vessel and comprising a plurality of elongated cutting members configured to cut material(s) inside the vessel, wherein the cage comprising a first end and a second end; wherein the first end, the second end, or both of the first and second ends, are moveable along the longitudinal axis of the shaft to change a distance between the first end and the second end of the cage; wherein the cage has a naturally expanded configuration when no external stress is imposed on the cage, the cage having a first cross sectional dimension when being in the naturally expanded configuration; wherein the cage is collapsible to form a collapsed configuration in response to an increase in the distance between the first end and the second end of the cage; and wherein the device further comprises a control configured to apply a radial force to expand the cage beyond its naturally expanded configuration so that the cage has a second cross sectional dimension that is larger than the first cross sectional dimension.

Optionally, the medical device further includes a filter coupled to the first end of the cage.

Optionally, the filter and the cage are configured to be simultaneously expandable and/or collapsible in response to relative movement(s) between the first end and the second end of the cage.

Optionally, a first cutting member of the cutting members extends from the first end of the cage to the second end of the cage in a helical configuration.

Optionally, a second cutting member of the cutting members extends from the first end of the cage to the second end of the cage in another helical configuration, and wherein at least a part of the first cutting member is parallel to at least a part of the second cutting member.

Optionally, the cutting members have respective cutting edges, each of the cutting edges facing a direction that is parallel to, or away from a wall of the vessel when the cage is in the naturally expanded configuration.

Optionally, the cutting members have respective cutting edges facing proximally.

Optionally, the cutting members have respective cutting edges facing distally.

Optionally, the medical device further includes a handle, wherein the control is implemented on the handle, and is configured to reduce and/or increase the distance between the first end and the second end of the cage.

Optionally, the medical device further includes a balloon coupled proximal to the cage, wherein the balloon is expandable for occluding the vessel.

Optionally, the medical device further includes a tube with a port, wherein the tube is configured to accommodate the cage, and the cage is moveable distally with respect to the tube to exit the tube via the port.

Optionally, the medical device further includes a balloon catheter with a lumen configured to accommodate at least a part of the tube.

Optionally, the shaft comprises an outer elongated member, and an inner elongated member disposed inside and slidable relative to the outer elongated member.

Optionally, the first end of the cage is coupled to the inner elongated member, and the second end of the cage is coupled to the outer elongated member.

Optionally, the inner elongated member has a solid cross section.

A medical device includes: a shaft having a longitudinal axis; a cage coupled to the shaft, the cage sized for placement in a vessel and comprising a plurality of elongated cutting members configured to cut material(s) inside the vessel, wherein the cage comprising a first end and a second end; and a filter coupled to the cage; wherein the first end, the second end, or both of the first and second ends, are moveable along the longitudinal axis of the shaft to change a distance between the first end and the second end of the cage; and wherein the filter and the cage are configured to be simultaneously expandable and/or collapsible in response to relative movement(s) between the first end and the second end of the cage.

Optionally, a first cutting member of the cutting members extends from the first end of the cage to the second end of the cage in a helical configuration.

Optionally, a second cutting member of the cutting members extends from the first end of the cage to the second end of the cage in another helical configuration, and wherein at least a part of the first cutting member is parallel to at least a part of the second cutting member.

Optionally, the cutting members have respective cutting edges, each of the cutting edges facing a direction that is parallel to, or away from a wall of the vessel when the cage is in an expanded configuration.

Optionally, the cutting members have respective cutting edges facing proximally.

Optionally, the cutting members have respective cutting edges facing distally.

Optionally, the medical device further includes a handle having a control, wherein the control is configured to reduce and/or increase the distance between the first end and the second end of the cage.

Optionally, the medical device further includes a balloon coupled proximal to the cage, wherein the balloon is expandable for occluding the vessel.

Optionally, the medical device further includes a tube with a port, wherein the tube is configured to accommodate the cage, and the cage is moveable distally with respect to the tube to exit the tube via the port.

Optionally, the medical device further includes a balloon catheter with a lumen configured to accommodate at least a part of the tube.

Optionally, the shaft comprises an outer elongated member, and an inner elongated member disposed inside and slidable relative to the outer elongated member.

Optionally, the first end of the cage is coupled to the inner elongated member, and the second end of the cage is coupled to the outer elongated member.

Optionally, the inner elongated member has a solid cross section.

Optionally, the cage has a naturally expanded configuration when no external stress is imposed on the cage, the cage having a first cross sectional dimension when being in the naturally expanded configuration; and wherein the medical device further comprises a control configured to apply a radial force to expand the cage beyond its naturally expanded configuration so that the cage has a second cross sectional dimension that is larger than the first cross sectional dimension.

A medical method includes: occluding a vessel via an expanded balloon that is coupled to a tube; assuming a naturally expanded configuration by a cage, the cage comprising a plurality of elongated cutting members, wherein the act of assuming the naturally expanded configuration is performed by the cage while the cage is in the vessel and while the cage is outside the tube, and wherein the cage has a first cross sectional dimension when it is in the naturally expanded configuration; assuming an enhanced expanded configuration by the cage, the enhanced expanded configuration having a second cross sectional dimension that is larger than the first cross sectional dimension; and cutting material(s) in the vessel via the elongated cutting members of the cage.

Optionally, the cage comprises a first end and a second end, and wherein the act of assuming the enhanced expanded configuration by the cage is performed in response to a decrease of distance between the first end and the second end of the cage.

Optionally, the method further includes catching the material(s) by a filter after the material(s) has been cut.

Optionally, the method further includes assuming an expanded configuration by the filter; wherein the act of assuming the expanded configuration by the filter and the act of assuming the naturally expanded configuration by the cage are performed simultaneously.

Optionally, the act of cutting the material(s) comprises using edges of the elongated cutting members, respectively, and wherein the edges of the elongated cutting members face proximally.

Optionally, the act of cutting the material(s) comprises using edges of the elongated cutting members, respectively, and wherein the edges of the elongated cutting members face distally.

Other and further aspects and features will be evident from reading the following detailed description.

DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only exemplary embodiments and are not therefore to be considered limiting in the scope of the claims.

FIG. 1 illustrates a medical device configured to remove material(s) in a vessel in accordance with some embodiments, particularly showing the medical device having a cage in a collapsed configuration.

FIG. 2 illustrates the medical device of FIG. 1, particularly showing the cage in its naturally expanded configuration.

DETAILED DESCRIPTION

Figure 3:
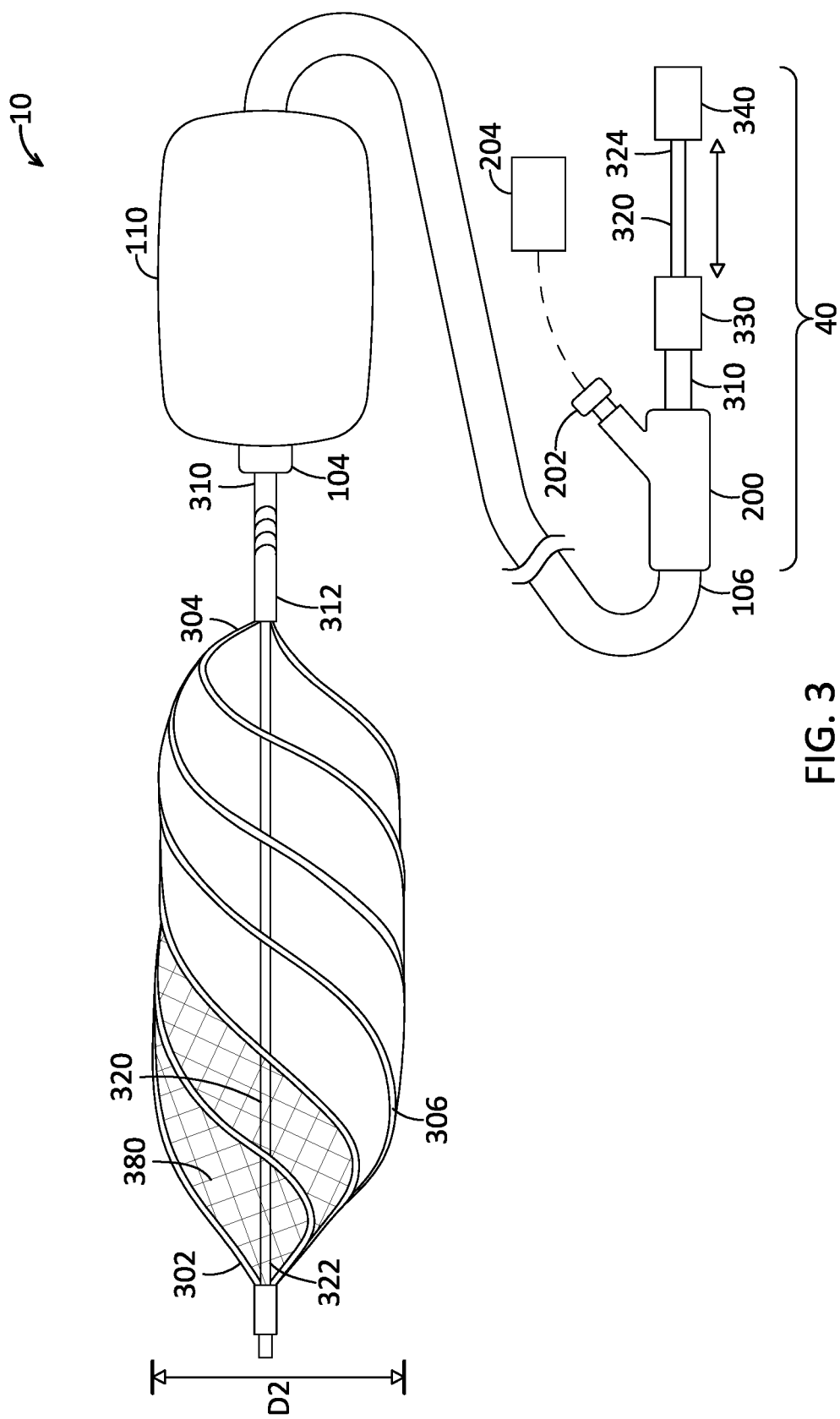
FIG. 3 illustrates the medical device of FIG. 1, particularly showing the cage in an enhanced expanded configuration.

Various embodiments are described hereinafter with reference to the figures. It should be noted that the figures are not drawn to scale and that elements of similar structures or functions are represented by the same reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

FIGS. 1-3 illustrate a medical device 10 configured to remove material(s) in a blood vessel lumen, in accordance with some embodiments of the disclosed inventions. The medical device 10 includes a tube 20, a cage 30 contained in the tube 20 and extendable out of the tube 20, a shaft 38 coupled to the cage 30, and a control 40 configured to manipulate the tube 20 and/or the cage 30.

The tube 20 has a distal end 104, a proximal end 106, and a body 108 extending between the distal end 104 and the proximal end 106. In the illustrated embodiments, the tube 20 also includes a balloon 110 at the distal end 104 of the tube 20. The proximal end 106 of the tube 20 is coupled to a hub 200 at the control 40. The hub 200 has a port 202 configured to receive fluid from a fluid source 204 for inflation of the balloon 110. The port 202 may also be configured to retrieve fluid from the balloon 110 to deflate the balloon 110. Alternatively, another port at the hub 200 may be configured to retrieve fluid from the balloon 110 to deflate the balloon 110. The balloon 110 is sized for occlusion of a vessel when the balloon 110 is inflated.

The cage 30 is sized for placement in a vessel. As shown in FIGS. 1-2, the cage 30 has a first end (distal end) 302, a second end (proximal end) 304, and a plurality of cutting members 306 configured to cut material(s) inside a vessel. As shown in FIG. 1, when the cage 30 is contained within the lumen 122 of the tube 20, the cage 30 is in a collapsed configuration. As shown in FIG. 2, when the cage 30 is deployed out of the distal end 104 of the tube 20 via a port 109, the cage 30 is in a naturally expanded configuration. When the cage 30 is in the naturally expanded configuration, no stress is imposed on the cage 30 (i.e., no outward radial force is applied externally to expand the cage 30), and the shape of the cage 30 in its naturally expanded configuration is due to the pre-formed shape of the cutting members 306 and their elasticity. As shown in FIG. 2, the cage 30 has a first cross sectional dimension D1 when being in the naturally expanded configuration. Because of the pre-formed shape of the cutting members 306 and their elasticity, the cage 30 acts as a spring that springs open to form the naturally expanded configuration when the cage 30 is deployed out of the tube 20. Such action by the cage 30 pulls the first end 302 of the cage 30 towards the second end 304 of the cage 30, pulls the second end 304 towards the first end 302, or pulls the first and second ends 302, 304 towards each other, thereby reducing a distance between the first end 302 of the cage 30 and the second end 304 of the cage 30.

Referring to FIGS. 1-2, the shaft 38 includes an outer elongated member 310, and an inner elongated member 320 located inside, and slidable relative to, the outer elongated member 310. The outer elongated member 310 has a distal end 312 to which the second end 304 of the cage 30 is coupled, and a proximal end 314 coupled to a first handle portion 330 of the control 40. The inner elongated member 320 has a distal end 322 to which the first end 302 of the cage 30 is coupled, and a proximal end 324 coupled to a second handle portion 340 of the control 40. In the illustrated embodiments, the inner elongated member 310 of the shaft 38 has a solid cross section along its length. In some cases, the inner elongated member 310 may be implemented using a wire. In other embodiments, the inner elongated member 310 of the shaft 38 may include one or more lumens.

In the illustrated embodiments, the first end 302 of the cage 30, the second end 304 of the cage 30, or both of the first and second ends 302, 304 of the cage 30, are moveable along the longitudinal axis of the shaft 38 to change a distance between the first end 302 and the second end 304 of the cage 30. For example, the cage 30 is collapsible to form the collapsed configuration in response to an increase in the distance between the first end 302 and the second end 304 of the cage 30. In particular, the first handle portion 330 and the second handle portion 340 of the control 40 may be manipulated by a user to increase the distance between the first end 302 and the second end 304 of the cage 30, thereby collapsing the cage 30 to create the collapsed configuration shown in FIG. 1. The cage 30 is also expandable beyond its naturally expanded configuration in response to a decrease in the distance between the first end 302 and the second end 304 of the cage 30. In particular, the first handle portion 330 and the second handle portion 340 of the control 40 may be manipulated by a user to apply a radial force to expand the cage 30 beyond its naturally expanded configuration so that the cage 30 has a second cross sectional dimension D2 that is larger than the first cross sectional dimension D1 (FIG. 3). As shown in FIG. 3, a distance between the first handle portion 330 and the second handle portion 340 is increased in order to reduce a distance between the first end 302 of the cage 30 and the second end 304 of the cage. This creates a radial force that urges the cage 30 to expand beyond its naturally expanded configuration.

It should be noted that the control 40 is not limited to the configuration shown, and that the control 40 may have other configurations in other embodiments. For example, in other embodiments, one or each of the first and second handle portions 330, 340 may be implemented as a shifter, a button, a knob, etc., on a handle. Also, in some embodiments, the hub 200 may be implemented as a part of a handle, or may be separate from the handle.

As shown in FIGS. 1-3, the medical device 10 further includes a filter 380 coupled to the first end 302 of the cage 30. In some cases, the filter 380 may be a soft and/or elastic mesh coupled to one or more of the cutting members 306. This is advantageous because it allows the filter 380 and the cage 30 to be simultaneously expandable and/or collapsible in response to relative movement(s) between the first end 302 and the second end 304 of the cage 30. Coupling the filter 380 to the cutting members 306 is also advantageous because as the cutting members 306 expand radially, the filter 380 will correspondingly also expand radially. This allows the size of the filter 380 to be automatically adjusted in response to a varying size of the cage 30. The filter 380 may be made from a variety of materials. By means of non-limiting examples, the filter 380 may be implemented using a polymer braid, a flashspun fabric, etc. Also, in some embodiments, the filter 380 may have a nose cone configuration.

In some embodiments, a first cutting member of the cutting members 306 extends from the first end 302 of the cage 30 to the second end 304 of the cage 30 in a helical configuration. Also, a second cutting member of the cutting members extends from the first end 302 of the cage 30 to the second end 304 of the cage 30 in another helical configuration, wherein at least a part of the first cutting member is parallel to at least a part of the second cutting member.

In some embodiments, the cutting members 306 have respective cutting edges, each of the cutting edges facing a direction that is parallel to, or away from a wall of the vessel when the cage 30 is in an expanded configuration. For example, in some embodiments, the cutting members 306 of the cage 30 have respective first cutting edges facing proximally. In such cases, after the cage 30 is deployed inside a vessel, moving the cage 30 proximally with respect to the vessel will cause the proximally facing cutting edges to cut into materials attached to the inner wall of the vessel. Alternatively or additionally, the cutting members 306 of the cage 30 have respective second cutting edges facing distally. In such cases, moving the cage 30 distally with respect to the vessel will cause the distally facing cutting edges to cut into the materials attached to the inner wall of the vessel.

Figure 4:
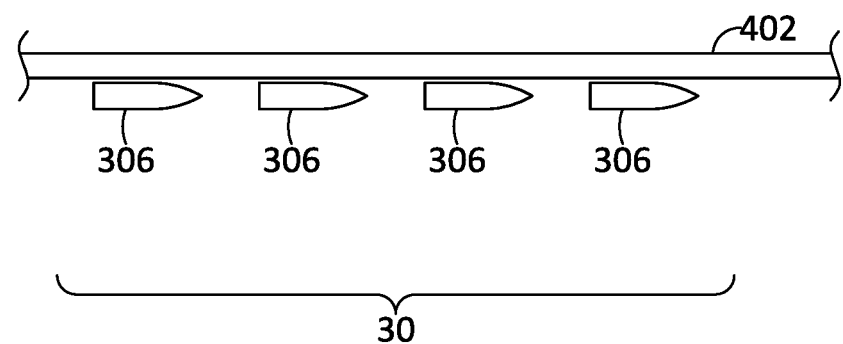
FIG. 4 illustrates a cross section of a part of the cage of FIG. 1, particularly showing cutting edges of cutting members of the cage facing in a direction that is parallel to a wall of a vessel.
Figure 5:
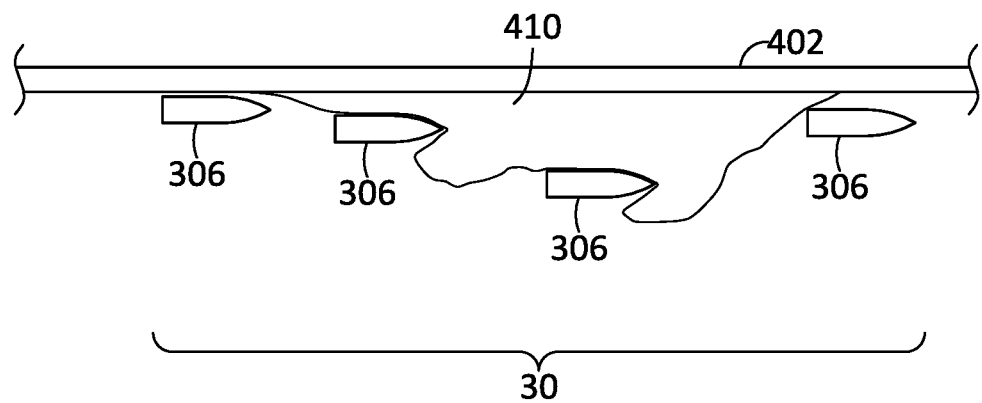
FIG. 5 illustrates a cross section of a part of the cage of FIG. 1, particularly showing the cutting edges of cutting members of the cage cutting into materials in a vessel.

As discussed, in some embodiments, when the cage 30 is in an expanded configuration, each of the cutting members 306 has a cutting edge facing only proximally or distally, or cutting edges facing both proximally and distally. This is beneficial in that it can prevent the cutting members 306 from cutting into a wall of the vessel. For example, as shown in FIG. 4, if the cutting members 306 have respective cutting edges facing only in the proximal direction, the cutting members 306 will not cut into the wall of the vessel even when they engage with the wall of the vessel. On the other hand, if the expanded cage 30 engages with materials along the wall of the vessel, the cutting edges of the cutting members 306 will cut into the materials (FIG. 5).

As shown in FIGS. 2-3, when the cage 30 is in the expanded configuration, the cutting members 306 are separated from each other to create an open porous body for the cage 30. This allows fluid (e.g., aspiration fluid, blood, etc.) to exit from within the cage 30 and/or to enter into the cage 30. Also, as shown in the figure, the cutting members 306 extend in an approximate parallel fashion so that the cutting members 306 do not cross each other. Such configuration is advantageous because it allows the materials in the vessel to more easily get in-between the cutting members 306, allowing the cutting members 306 to more effectively cut the materials in the vessel. In other embodiments, one or more cutting members 306 may cross other cutting member(s) 306. For example, in other embodiments, the cutting members 306 may form a grid configuration.

It should be noted that the medical device 100 is not limited to the features and configurations described in the above embodiments, and that the medical device 100 may have other features and configurations in other embodiments. For example, in other embodiments, the tube 20 may not include the balloon 110, and the control 40 may not include the hub 200. In further embodiments, the medical device 100 may not include the tube 20. In other embodiments, the medical device 100 may not include the filter 380. In still further embodiments, the inner elongated member 320 of the shaft 38 may have one or more lumens, which may be utilized for housing a guidewire, delivery of a substance (e.g., drug, saline, aspiration fluid, etc.), and/or removal of a substance from inside a patient.

In addition, in other embodiments, the medical device 100 may optionally further include a sheath configured to contain the cage 30. In such cases, the sheath may be disposed inside the lumen 122 of the tube 20, and is slidable relative to the tube 20. During use, the sheath containing the cage 30 may be advanced distally so that a distal portion of the sheath will move out of the port 109 at the distal end 104 of the tube 20. After the distal portion of the sheath (containing the cage 30 in its collapsed configuration) exits out of the tube 20, the cage 30 may then be deployed out of the sheath so that the cage 30 can expand into an expanded configuration. Such may be accomplished by retracting the sheath proximally relative to the cage 30, or by advancing the cage 30 distally relative to the sheath.

Also, in other embodiments, the distal end 104 of the tube 20, and/or a distal end of the sheath (if the medical device 10 includes the sheath), may have a sharp tip configured to pierce tissue and/or materials in the vessel.

In addition, in other embodiments, the medical device 10 may include a steering mechanism configured to steer the distal end 104 of the tube 20, or the distal end of the sheath (if the medical device 10 includes the sheath). The steering mechanism may include one or more steering wires coupled to the distal end of the tube 20 or the sheath for applying tension to thereby bend the distal end of the tube 20 or the sheath. In such cases, the control 40 may include a button, a knob, a slider, etc., for allowing the user to apply tension to the steering wire(s).

Furthermore, in the above embodiments, the cage 30 is described as having a naturally expanded configuration. In other embodiments, the cage 30 may not have a naturally expanded configuration. Instead, the cage 30 may have a collapsed configuration (like that shown in FIG. 1) that is its naturally relaxed configuration. In such cases, after the cage 30 is deployed out of the tube 20, the cage 30 will not spring open automatically. Instead, the cage 30 will remain in the collapsed configuration. The first handle portion 330 and/or the second handle portion 340 may be manipulated to apply a radial force to expand the cage 30 from its collapsed configuration. During use, the first handle portion 330 and/or the second handle portion 340 may be repeatedly manipulated to vary the size of the cage 30 in order to adjust an amount of force being exerted by the cage 30 towards the wall of the vessel or towards the materials in the vessel.

Figure 6:
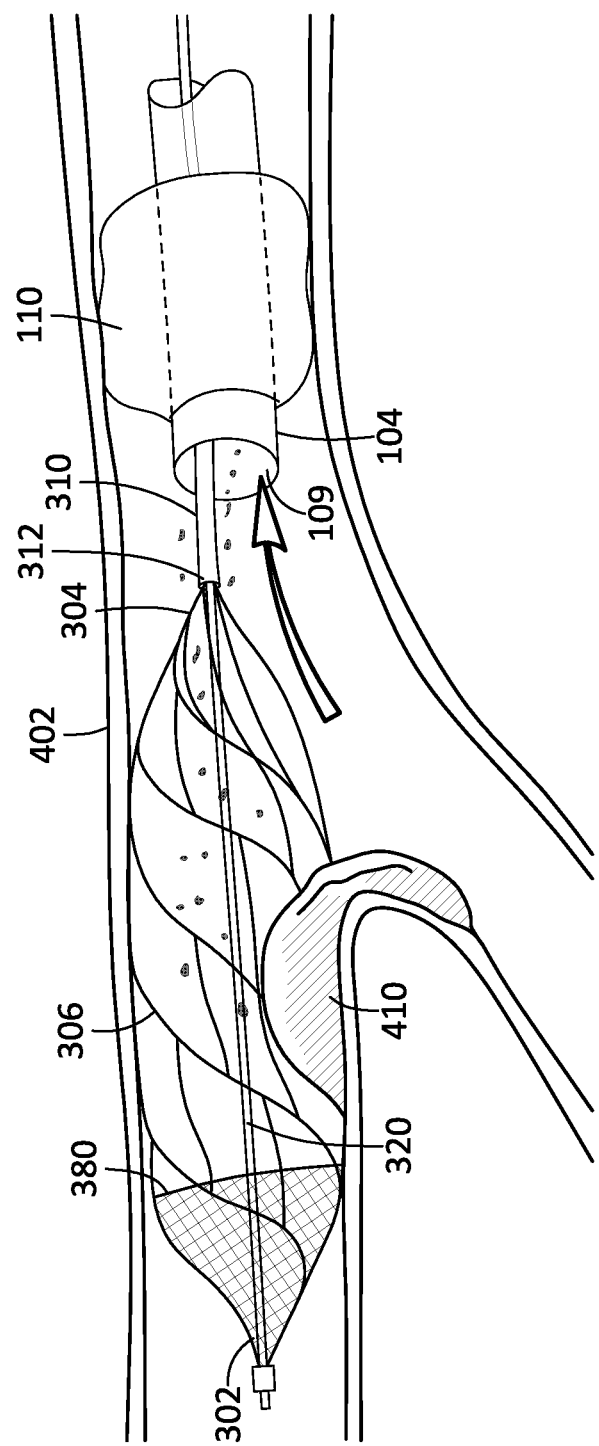
FIG. 6 illustrates the medical device of FIG. 1 being used in a vessel to remove material(s).

The medical device 10 of FIG. 1 may be used in a vessel to remove material(s). First, the tube 20 of the medical device 10 is inserted into a vessel of a patient, and is advanced until the distal end 104 of the tube 20 reaches the target site in the vessel. As shown in FIG. 6, the distal end 104 of the tube 20 may be placed inside the vessel 402 proximally with respect to material(s) 410 to be removed.

Various techniques may be utilized to insert and position the distal end 104 of the tube 20 at the target site. In some cases, if the tube 20 is steerable, the distal end 104 of the tube 20 may steered as the tube 20 is being advanced within the vessel 402 to reach the target site in the vessel 402. Alternatively, a guidewire may first be inserted into the vessel 402, and the guidewire is advanced to the target site in the vessel 402 that contains material(s) to be removed. After the guidewire has been desirably positioned, the tube 20 may then be disposed (slided) over the guidewire and be advanced distally. As the tube 20 is being advanced, the guidewire functions as a guide/steering mechanism to guide the distal end 104 of the tube 20 to the target site in the vessel 402.

As shown in FIG. 6, after the distal end 104 of the tube 20 has been desirably positioned, inflation fluid from the fluid source 204 is delivered, via the port 202, to inflate the balloon 110 at the distal end 104 of the tube 20. The inflated balloon 110 occludes the vessel that is to be treated. In some cases, the inflated balloon 110 arrests blood flow proximal to a lesion to be removed in a vessel.

When the tube 20 is inside the vessel, the cage 30 initially is contained within the tube 20 so that the cage 30 has the collapsed configuration, like that shown in FIG. 1. Next, the cage 30 in the tube 20 is advanced distally to exit the distal end 104 of the tube 20. Such may be accomplished by manually advancing the second handle portion 340, or advancing both the first and second handle portions 330, 340, relative to the hub 200 at the control 40. After the cage 30 exits out of the tube 20, the cage 30 automatically assumes its naturally expanded configuration due to the inherent shape of the cage 30, like that shown in FIG. 2. In some embodiments, the cross-sectional dimension D1 of the naturally expanded configuration is less than a diameter of the vessel lumen. In some cases, in order to place the cage 30 distally with respect to the material(s) 410, the control 40 may be operated to collapse the cage 30 while the cage 30 is outside the tube 20. For example, the second handle portion 340 may be advanced distally towards the first handle portion 330, or the first handle portion 330 may be retracted proximally towards the second handle portion 340, to increase a distance between the first end 302 of the cage 30 and the second end 304 of the cage, thereby collapsing the cage 30. The collapsed cage 30 may then be advanced distally until it has traversed the material(s) 410 to reach a location that is distal to the material(s) 410. Next, the manipulating force applied by the user on the first handle portion 330 and/or the second handle portion 340 may be released to allow the cage 30 to assume its naturally expanded configuration while the cage 30 is distal to the material(s) 410.

In other embodiments, if the cage 30 does not have a naturally expanded configuration, after the cage 30 is deployed outside the tube 20, the cage 30 will continue to have the collapsed configuration. In such cases, the cage 30 in its collapsed configuration may be advanced distally until it has traversed the material(s) 410 to reach a location that is distal to the material(s) 410. Then the control 40 may be manipulated to expand the cage 30 while the cage 30 is distal to the material(s) 410.

In other cases, if the medical device 10 includes an additional sheath containing the cage 30, the sheath with the cage 30 in its collapsed configuration may be advanced distally relative to the tube 20 to exit out of the tube 20. The distal end of the sheath and the cage 30 contained therein may be advanced distally so that the distal end of the sheath and the cage 30 are distal relative to the material(s) 410. Next, the sheath may be retracted to deploy the cage 30 out of the sheath, resulting in the deployed cage 30 being distal to the material(s) 410.

Next, the cage 30 is moved proximally with respect to the vessel to cut the material(s) 410 along an inner wall of the vessel 402 (FIG. 6). Such may be accomplished by moving the first handle portion 330, or both of the first and second handle portions 330, 340 (shown in FIGS. 1-3), proximally relative to the hub 200 at the control 40.

In some cases, if the cutting elements 306 of the cage 30 have distally facing cutting edges, the cage 30 may also be moved distally with respect to the vessel to cut the material(s) 410 along the inner wall of the vessel 402. Such may be accomplished by moving the first handle portion 330, or both of the first and second handle portions 330, 340, distally relative to the hub 200 at the control 40.

In some cases, if the cross sectional dimension D1 of the naturally expanded configuration of the cage 30 is less than a diameter of the lumen of the vessel 402, the cage 30 may be expanded beyond its naturally expanded configuration, so that the cage 30 has a larger cross sectional dimension D2 than the cross sectional dimension D1 (like that shown in FIG. 3). In particular, the second handle portion 340 may be moved proximally relative to the first handle portion 330 to pull the first end 302 of the cage 30 towards the second end 304 of the cage 30. This creates an outward radial force to cause the cage 30 to expand further beyond its naturally expanded configuration.

Also, in some cases, if the naturally expanded configuration of the cage 30 already abuts the inner wall of the vessel 402 circumferentially, the cage 30 may still be expanded beyond its naturally expanded configuration to increase the abutment force imposed by the cage 30 towards the inner wall of the vessel 402. Such technique may allow the cage 30 to be used to cut materials 410 that are closer to the inner wall of the vessel 402.

In addition, in one technique of use of the medical device 10, the radial expansion force by the cage 30 against the wall of the vessel 402 may be selectively adjusted while the cage 30 is being used to cut the material(s) 410. For example, the user of the medical device 10 may increase the abutment force imposed by the cage 30 towards the material(s) 410 or the wall of the vessel 402 by pulling the second handle portion 340 proximally relative to the first handle portion 330, or by advancing the first handle portion 330 distally relative to the second handle portion 340. This has the effect of bringing the first end 302 and the second end 304 of the cage 30 closer to each other to urge the cage 30 to expand radially. As a result, more material(s) 410 may get in-between the cutting members 306, allowing more material(s) 410 to be cut away from the vessel wall. Therefore, the control 40 may be utilized to adjust an amount (e.g., thickness) of the material(s) 410 that is desired to be cut from the vessel 402.

As the cage 30 cuts away material(s) 410 from the vessel 402, the cut material(s) 410 are caught by the filter 380, which prevents the material(s) 410 from travelling away from the target site in the vessel 402. Because the filter 380 is coupled to the cutting elements 306 of the cage 30, regardless of the size of the cage 30 created during use of the medical device 10, the size of the filter 380 will correspondingly change to match the size (e.g., cross sectional dimension) of the cage 30.

In some embodiments, the port 109 at the distal end 104 of the tube may be utilized to collect the cut materials 410, debris, aspiration fluid, and/or blood. Alternatively, another suction tube may be provided in the tube 20 to collect the cut materials 410, debris, aspiration fluid, and/or blood from inside the vessel.

Figure 7:
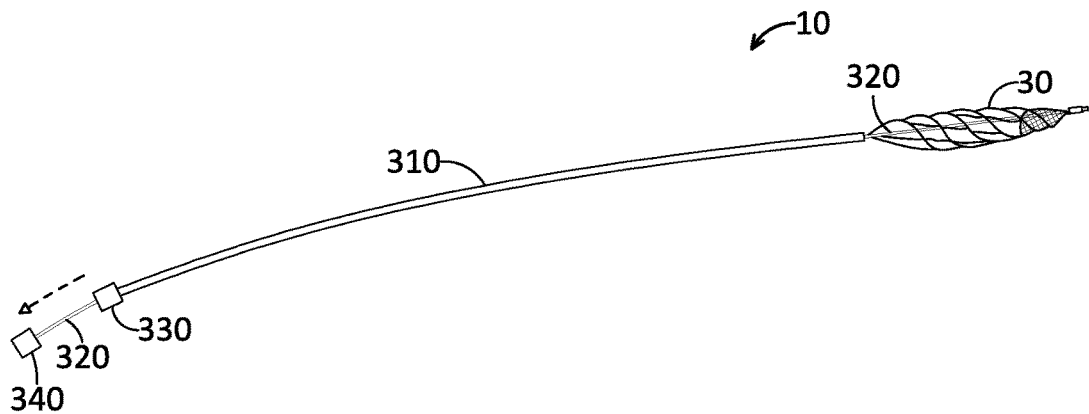
FIG. 7 illustrates another medical device.

It should be noted that the medical device 10 is not limited to the exemplary features and configurations described in the previous embodiments, and that the medical device 10 may have other features and/or configurations. For example, in other embodiments, the medical device 10 may not include the tube 20. Instead, the medical device 10 may just include the cage 30 coupled to the handles 330, 340 via respective elongated members 310, 320 (FIG. 7). In such cases, the medical device 10 may be inserted into another device (e.g., a catheter, such as a microcatheter, a balloon catheter, etc.) during use. In some embodiments, the elongated member 320 may be stiff enough to provide tension and/or compression during use.

Figure 8:
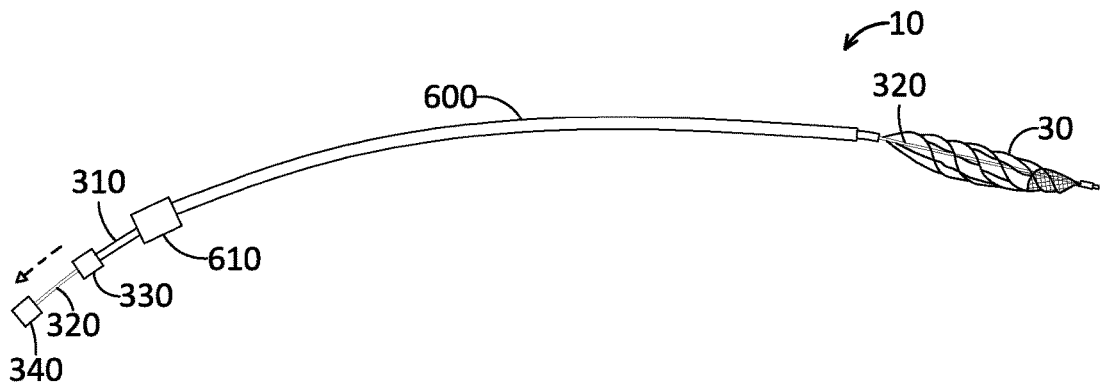
FIG. 8 illustrates the medical device of FIG. 7, further including a catheter/tube.

Also, in other embodiments, the medical device 10 of FIG. 7 may further include a catheter (tube) 600 for housing the cage 30 and the elongated member 310 (FIG. 8). The catheter 600 may include a handle 610 for allowing manipulation by a user. During use, the cage 30 may be deployed out of a distal end of the catheter 600 by distally advancing the handle 330 relative to the handle 610. In some embodiments, the catheter 600 may be a microcatheter.

Figure 9:
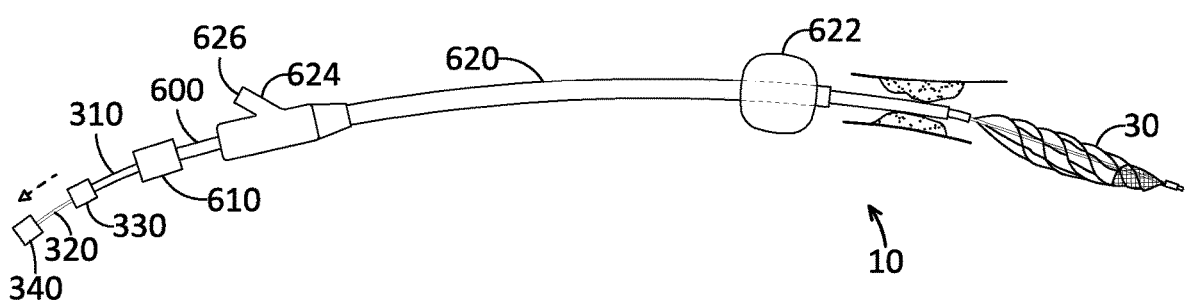
FIG. 9 illustrates the medical device of FIG. 8, further including a balloon catheter.

In further embodiments, the medical device 10 of FIG. 8 may further include a balloon catheter 620 (FIG. 9). The balloon catheter 620 includes an inflatable balloon 622 configured to occlude a blood vessel when inflated, and a handle 624 with a port 626 for receiving inflation fluid to inflate the balloon 622. The balloon catheter 620 is configured for housing the catheter/tube 600 of FIG. 7, with the catheter/tube 600 accommodating the cage 30. During use, a distal segment of the catheter/tube 600 containing the cage 30 may be deployed out of the balloon catheter 620 by advancing the handle 610 distally with respect to the handle 624 of the balloon catheter 620, while the cage 30 is contained inside the catheter/tube 600. Then the cage 30 may be deployed out of the distal end of the catheter/tube 600. Such may be accomplished by retracting the catheter/tube 600 proximally relative to the cage 30, or by advancing the cage 30 distally relative to the catheter/tube 600. The medical device 10 of FIG. 9 is advantageous because it allows a deployment location of the cage 30 to be adjusted even after the balloon 622 is inflated and is secured inside a vessel. In other embodiments, the medical device 10 may not include the catheter/tube 600, and the balloon catheter 620 may be configured to directly house the cage 30 and the elongated member 310 without the catheter/tube 600.

Figure 10:
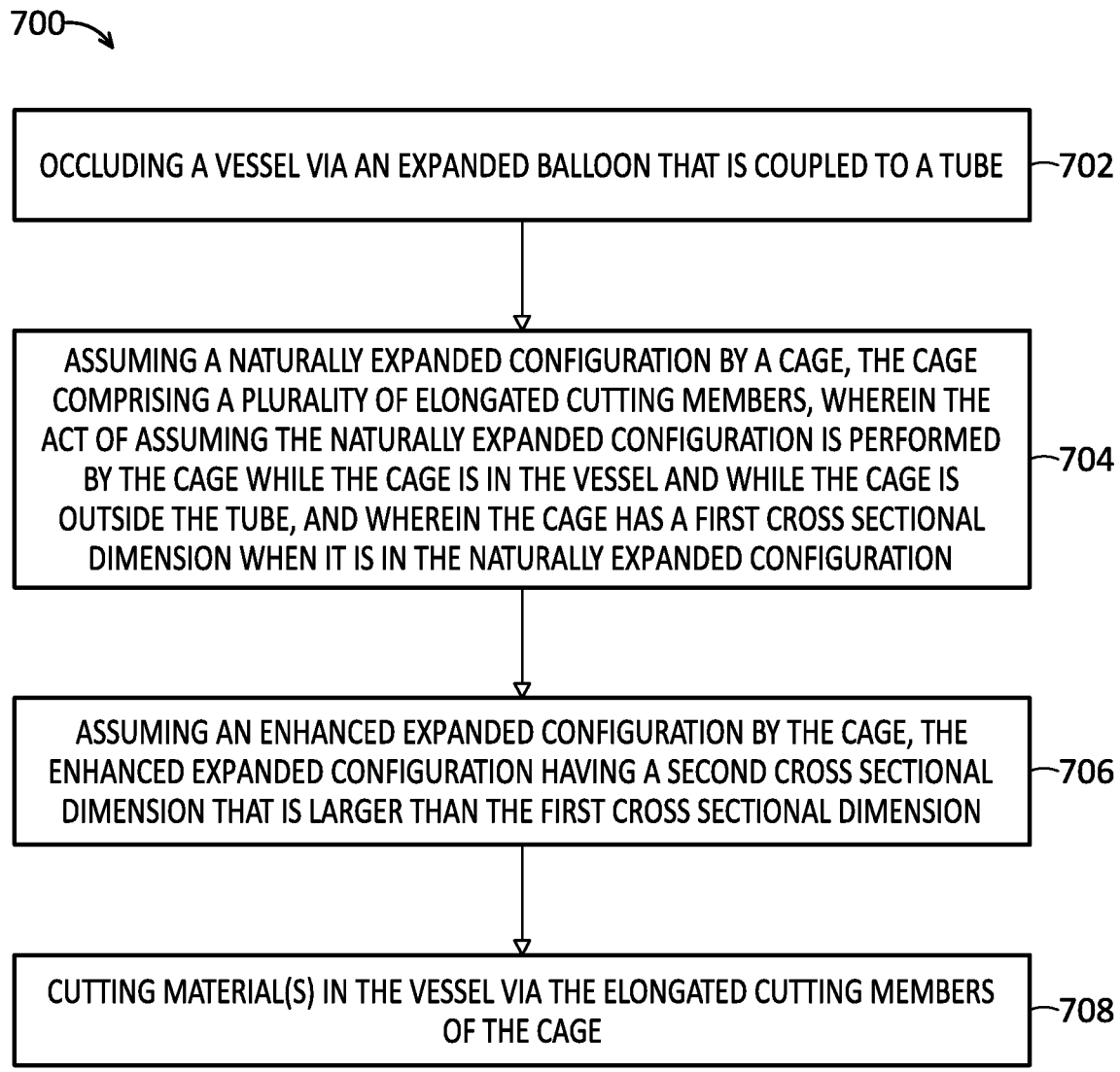
FIG. 10 illustrates a method of removing material(s) in a vessel in accordance with some embodiments.

FIG. 10 illustrates a method 700 of removing material(s) in a vessel in accordance with some embodiments. The method 700 includes occluding a vessel via an expanded balloon that is coupled to a tube (item 702). The method 700 also includes assuming a naturally expanded configuration by a cage, the cage comprising a plurality of elongated cutting members, wherein the act of assuming the naturally expanded configuration is performed by the cage while the cage is in the vessel and while the cage is outside the tube, and wherein the cage has a first cross sectional dimension when it is in the naturally expanded configuration (item 704). The method 700 further includes assuming an enhanced expanded configuration by the cage, the enhanced expanded configuration having a second cross sectional dimension that is larger than the first cross sectional dimension; and cutting material(s) in the vessel via the elongated cutting members of the cage (item 706).

Optionally, in the method 700, the cage comprises a first end and a second end, and wherein the act of assuming the enhanced expanded configuration by the cage is performed in response to a decrease of distance between the first end and the second end of the cage.

Optionally, the method 700 further includes catching the material(s) by a filter after the material(s) has been cut.

Optionally, the method 700 further includes assuming an expanded configuration by the filter; wherein the act of assuming the expanded configuration by the filter and the act of assuming the naturally expanded configuration by the cage are performed simultaneously.

Optionally, in the method 700, the act of cutting the material(s) comprises using edges of the elongated cutting members, respectively, and wherein the edges of the elongated cutting members face proximally.

Optionally, in the method 700, the act of cutting the material(s) comprises using edges of the elongated cutting members, respectively, and wherein the edges of the elongated cutting members face distally.

The following items are exemplary features of embodiments described herein. Each item may be an embodiment itself or may be a part of an embodiment. One or more items described below may be combined with other item(s) in an embodiment.

Item 1: A medical device includes: a shaft having a longitudinal axis; and a cage coupled to the shaft, the cage sized for placement in a vessel and comprising a plurality of elongated cutting members configured to cut material(s) inside the vessel, wherein the cage comprising a first end and a second end; wherein the first end, the second end, or both of the first and second ends, are moveable along the longitudinal axis of the shaft to change a distance between the first end and the second end of the cage; wherein the cage has a naturally expanded configuration when no external stress is imposed on the cage, the cage having a first cross sectional dimension when being in the naturally expanded configuration; wherein the cage is collapsible to form a collapsed configuration in response to an increase in the distance between the first end and the second end of the cage; and wherein the medical device further comprises a control configured to apply a radial force to expand the cage beyond its naturally expanded configuration so that the cage has a second cross sectional dimension that is larger than the first cross sectional dimension.

Item 2: The medical device further includes a filter coupled to the first end of the cage.

Item 3: In the medical device, the filter and the cage are configured to be simultaneously expandable and/or collapsible in response to relative movement(s) between the first end and the second end of the cage.

Item 4: In the medical device, a first cutting member of the cutting members extends from the first end of the cage to the second end of the cage in a helical configuration.

Item 5: In the medical device, a second cutting member of the cutting members extends from the first end of the cage to the second end of the cage in another helical configuration, and wherein at least a part of the first cutting member is parallel to at least a part of the second cutting member.

Item 6: In the medical device, the cutting members have respective cutting edges, each of the cutting edges facing a direction that is parallel to, or away from a wall of the vessel when the cage is in the naturally expanded configuration.

Item 7: In the medical device, the cutting members have respective cutting edges facing proximally.

Item 8: In the medical device, the cutting members have respective cutting edges facing distally.

Item 9: The medical device further includes a handle, wherein the control is implemented on the handle, and is configured to reduce and/or increase the distance between the first end and the second end of the cage.

Item 10: The medical device further includes a balloon coupled proximal to the cage, wherein the balloon is expandable for occluding the vessel.

Item 11: The medical device further includes a tube with a port, wherein the tube is configured to accommodate the cage, and the cage is moveable distally with respect to the tube to exit the tube via the port.

Item 12: The medical device further includes a balloon catheter with a lumen configured to accommodate at least a part of the tube.

Item 13: In the medical device, the shaft comprises an outer elongated member, and an inner elongated member disposed inside and slidable relative to the outer elongated member.

Item 14: In the medical device, the first end of the cage is coupled to the inner elongated member, and the second end of the cage is coupled to the outer elongated member.

Item 15: In the medical device, the inner elongated member has a solid cross section.

Item 16: A medical device includes: a shaft having a longitudinal axis; a cage coupled to the shaft, the cage sized for placement in a vessel and comprising a plurality of elongated cutting members configured to cut material(s) inside the vessel, wherein the cage comprising a first end and a second end; and a filter coupled to the cage; wherein the first end, the second end, or both of the first and second ends, are moveable along the longitudinal axis of the shaft to change a distance between the first end and the second end of the cage; and wherein the filter and the cage are configured to be simultaneously expandable and/or collapsible in response to relative movement(s) between the first end and the second end of the cage.

Item 17: In the medical device, a first cutting member of the cutting members extends from the first end of the cage to the second end of the cage in a helical configuration.

Item 18: In the medical device, a second cutting member of the cutting members extends from the first end of the cage to the second end of the cage in another helical configuration, and wherein at least a part of the first cutting member is parallel to at least a part of the second cutting member.

Item 19: In the medical device, the cutting members have respective cutting edges, each of the cutting edges facing a direction that is parallel to, or away from a wall of the vessel when the cage is in an expanded configuration.

Item 20: In the medical device, the cutting members have respective cutting edges facing proximally.

Item 21: In the medical device, the cutting members have respective cutting edges facing distally.

Item 22: The medical device further includes a handle having a control, wherein the control is configured to reduce and/or increase the distance between the first end and the second end of the cage.

Item 23: The medical device further includes a balloon coupled proximal to the cage, wherein the balloon is expandable for occluding the vessel.

Item 24: The medical device further includes a tube with a port, wherein the tube is configured to accommodate the cage, and the cage is moveable distally with respect to the tube to exit the tube via the port.

Item 25: The medical device further includes a balloon catheter with a lumen configured to accommodate at least a part of the tube.

Item 26: In the medical device, the shaft comprises an outer elongated member, and an inner elongated member disposed inside and slidable relative to the outer elongated member.

Item 27: In the medical device, the first end of the cage is coupled to the inner elongated member, and the second end of the cage is coupled to the outer elongated member.

Item 28: In the medical device, the inner elongated member has a solid cross section.

Item 29: In the medical device, the cage has a naturally expanded configuration when no external stress is imposed on the cage, the cage having a first cross sectional dimension when being in the naturally expanded configuration; and wherein the medical device further comprises a control configured to apply a radial force to expand the cage beyond its naturally expanded configuration so that the cage has a second cross sectional dimension that is larger than the first cross sectional dimension.

Item 30: A medical method includes: occluding a vessel via an expanded balloon that is coupled to a tube; assuming a naturally expanded configuration by a cage, the cage comprising a plurality of elongated cutting members, wherein the act of assuming the naturally expanded configuration is performed by the cage while the cage is in the vessel and while the cage is outside the tube, and wherein the cage has a first cross sectional dimension when it is in the naturally expanded configuration; assuming an enhanced expanded configuration by the cage, the enhanced expanded configuration having a second cross sectional dimension that is larger than the first cross sectional dimension; and cutting material(s) in the vessel via the elongated cutting members of the cage.

Item 31: In the method, the cage comprises a first end and a second end, and wherein the act of assuming the enhanced expanded configuration by the cage is performed in response to a decrease of distance between the first end and the second end of the cage.

Item 32: The method further includes catching the material(s) by a filter after the material(s) has been cut.

Item 33: The method further includes assuming an expanded configuration by the filter; wherein the act of assuming the expanded configuration by the filter and the act of assuming the naturally expanded configuration by the cage are performed simultaneously.

Item 34: In the method, the act of cutting the material(s) comprises using edges of the elongated cutting members, respectively, and wherein the edges of the elongated cutting members face proximally.

Item 35: In the method, the act of cutting the material(s) comprises using edges of the elongated cutting members, respectively, and wherein the edges of the elongated cutting members face distally.

Thus, it will be appreciated that, in addition to the various embodiments of the medical devices disclosed herein, further disclosed are methods of using such devices for removing materials from within blood vessel lumens, including without limitation, one method including the acts of occluding a vessel via an expanded balloon that is coupled to a tube; assuming a naturally expanded configuration by a cage, the cage comprising a plurality of elongated cutting members, wherein the act of assuming the naturally expanded configuration is performed by the cage while the cage is in the vessel and while the cage is outside the tube, and wherein the cage has a first cross sectional dimension when it is in the naturally expanded configuration; assuming an enhanced expanded configuration by the cage, the enhanced expanded configuration having a second cross sectional dimension that is larger than the first cross sectional dimension; and cutting material(s) in the vessel via the elongated cutting members of the cage. The cage may comprise a first end and a second end, and wherein the act of assuming the enhanced expanded configuration by the cage is performed in response to a decrease of distance between the first end and the second end of the cage. The method may further include catching the material(s) by a filter after the material(s) has been cut. The method may further include assuming an expanded configuration by the filter, wherein the act of assuming the expanded configuration by the filter and the act of assuming the naturally expanded configuration by the cage are performed simultaneously. The act of cutting the material(s) may include using edges of the elongated cutting members, respectively, and wherein the edges of the elongated cutting members face proximally or distally.

Although particular embodiments have been shown and described, it will be understood that it is not intended to limit the claimed inventions to the preferred embodiments, and it will be obvious to those skilled in the art that various changes and modifications may be made without department from the spirit and scope of the claimed inventions. The specification and drawings are, accordingly, to be regarded in an illustrative rather than restrictive sense. The claimed inventions are intended to cover alternatives, modifications, and equivalents.

What is claimed is:

1. A medical device, comprising:
   a shaft having a longitudinal axis; and
   a cage coupled to the shaft, the cage sized for placement in a vessel and comprising a plurality of elongated cutting members configured to cut material(s) inside the vessel, wherein the cage comprising a first end and a second end;
   wherein the first end, the second end, or both of the first and second ends, are moveable along the longitudinal axis of the shaft to change a distance between the first end and the second end of the cage;
   wherein the cage has a naturally expanded configuration when no external stress is imposed on the cage, the cage having a first cross sectional dimension when being in the naturally expanded configuration;
   wherein the cage is collapsible to form a collapsed configuration in response to an increase in the distance between the first end and the second end of the cage;
   wherein the medical device further comprises a control configured to apply a radial force to expand the cage beyond its naturally expanded configuration so that the cage has a second cross sectional dimension that is larger than the first cross sectional dimension; and
   wherein at least one of the cutting members has first and second cutting edges, the first cutting edge facing a first direction that is parallel to, or that forms an acute angle with, a wall of the vessel when the cage is in the naturally expanded configuration, wherein the first direction has a first directional component pointing proximally, and wherein the second cutting edge faces a second direction with a second directional component pointing distally.

2. The medical device of claim 1, further comprising a filter coupled to the first end of the cage.

3. The medical device of claim 2, wherein the filter and the cage are configured to be simultaneously expandable and/or collapsible in response to relative movement(s) between the first end and the second end of the cage.

4. The medical device of claim 1, wherein a first cutting member of the cutting members extends from the first end of the cage to the second end of the cage in a helical configuration.

5. The medical device of claim 4, wherein a second cutting member of the cutting members extends from the first end of the cage to the second end of the cage in another helical configuration, and wherein at least a part of the first cutting member is parallel to at least a part of the second cutting member.

6. The medical device of claim 1, wherein the direction has a directional component facing proximally.

7. The medical device of claim 1, wherein the direction has a directional component facing distally.

8. The medical device of claim 1, further comprising a handle, wherein the control is implemented on the handle, and is configured to reduce and/or increase the distance between the first end and the second end of the cage.

9. The medical device of claim 1, further comprising a balloon coupled proximal to the cage, wherein the balloon is expandable for occluding the vessel.

10. The medical device of claim 1, further comprising a tube with a port, wherein the tube is configured to accommodate the cage, and the cage is moveable distally with respect to the tube to exit the tube via the port.

11. The medical device of claim 10, further comprising a balloon catheter with a lumen configured to accommodate at least a part of the tube.

12. The medical device of claim 1, wherein the shaft comprises an outer elongated member, and an inner elongated member disposed inside and slidable relative to the outer elongated member.

13. The medical device of claim 12, wherein the first end of the cage is coupled to the inner elongated member, and the second end of the cage is coupled to the outer elongated member.

14. The medical device of claim 12, wherein the inner elongated member has a solid cross section.

15. A medical device, comprising:
a shaft having a longitudinal axis;
a cage coupled to the shaft, the cage sized for placement in a vessel and comprising a plurality of elongated cutting members configured to cut material(s) inside the vessel, wherein the cage comprising a first end and a second end; and
a filter coupled to the cage;
wherein the first end, the second end, or both of the first and second ends, are moveable along the longitudinal axis of the shaft to change a distance between the first end and the second end of the cage;
wherein the filter and the cage are configured to be simultaneously expandable and/or collapsible in response to relative movement(s) between the first end and the second end of the cage;
wherein the cutting members have respective cutting edges, at least one of the cutting edges facing a direction that is parallel to, or that forms an acute angle with, a wall of the vessel when the cage is in an expanded configuration;
wherein the medical device further comprises a tube with a port, wherein the tube is configured to accommodate the cage, and the cage is moveable distally with respect to the tube to exit the tube via the port, and wherein the medical device further comprises a balloon catheter with a lumen configured to accommodate at least a part of the tube;
wherein the shaft comprises an outer elongated member, and an inner elongated member disposed inside and slidable relative to the outer elongated member; and
wherein the first end of the cage is coupled to the inner elongated member, and the second end of the cage is coupled to the outer elongated member, and wherein the inner elongated member has a solid cross section.

16. The medical device of claim 15, wherein a first cutting member of the cutting members extends from the first end of the cage to the second end of the cage in a helical configuration.

17. The medical device of claim 16, wherein a second cutting member of the cutting members extends from the first end of the cage to the second end of the cage in another helical configuration, and wherein at least a part of the first cutting member is parallel to at least a part of the second cutting member.

18. The medical device of claim 15, wherein the direction has a directional component facing proximally.

19. The medical device of claim 15, wherein the direction has a directional component facing distally.

20. The medical device of claim 15, further comprising a handle having a control, wherein the control is configured to reduce and/or increase the distance between the first end and the second end of the cage.

21. The medical device of claim 15, further comprising a balloon, wherein the balloon is expandable for occluding the vessel.

22. The medical device of claim 15, wherein the cage has a naturally expanded configuration when no external stress is imposed on the cage, the cage having a first cross sectional dimension when being in the naturally expanded configuration; and
wherein the medical device further comprises a control configured to apply a radial force to expand the cage beyond its naturally expanded configuration so that the cage has a second cross sectional dimension that is larger than the first cross sectional dimension.

* * * * *